(12) United States Patent
Kassner

(10) Patent No.: US 9,097,696 B2
(45) Date of Patent: Aug. 4, 2015

(54) DEVICE FOR MEASURING A COMPOSITION OF A FUEL MIXTURE

(75) Inventors: Uwe Kassner, Moeglingen (DE); Bettina Kassner, legal representative, Moeglingen (DE); Milena Kassner, legal representative, Moeglingen (DE)

(73) Assignee: ROBERT BOSCH GMBH, Stuttgart (DE)

( * ) Notice: Subject to any disclaimer, the term of this patent is extended or adjusted under 35 U.S.C. 154(b) by 329 days.

(21) Appl. No.: 13/516,608

(22) PCT Filed: Nov. 25, 2010

(86) PCT No.: PCT/EP2010/068248
§ 371 (c)(1),
(2), (4) Date: Aug. 31, 2012

(87) PCT Pub. No.: WO2011/082884
PCT Pub. Date: Jul. 14, 2011

(65) Prior Publication Data
US 2013/0133406 A1    May 30, 2013

(30) Foreign Application Priority Data

Dec. 17, 2009   (DE) .......................... 10 2009 054 844

(51) Int. Cl.
*G01N 33/20*  (2006.01)
*G01N 33/28*  (2006.01)

(52) U.S. Cl.
CPC ........ *G01N 33/2835* (2013.01); *G01N 33/2847* (2013.01); *G01N 33/2852* (2013.01)

(58) Field of Classification Search
CPC ....................... G01N 33/2835; G01N 33/2852
USPC .......................................................... 73/61.43
See application file for complete search history.

(56) References Cited

U.S. PATENT DOCUMENTS

| 4,945,863 | A | 8/1990 | Schmitz et al. |
| 5,488,311 | A | 1/1996 | Kamioka et al. |
| 5,973,503 | A | 10/1999 | Kuipers et al. |

FOREIGN PATENT DOCUMENTS

| CN | 1830112 | 9/2006 |
| CN | 101169388 | 4/2008 |
| CN | 101435836 | 5/2009 |
| CN | 101551354 | 10/2009 |
| CN | 101680852 | 3/2010 |
| CN | 101802376 | 8/2010 |
| DE | 34 12 704 | 10/1984 |
| DE | 4117913 | 12/1991 |
| DE | 10 2007 039861 | 2/2009 |
| EP | 0 377 782 | 7/1990 |
| EP | 0 819 938 | 1/1998 |

*Primary Examiner* — Laura Martin
*Assistant Examiner* — Alex Devito
(74) *Attorney, Agent, or Firm* — Kenyon & Kenyon LLP

(57) ABSTRACT

A method and a device for determining a composition of a fuel mixture, in particular for determining the ethanol content and/or a water component in the fuel mixture. Fuel flows sequentially through spatially separated sensor elements. The sensor elements generate time-dependent output signals, which are unambiguously dependent on the ethanol content of the fuel mixture. A difference between the time-dependent output signals is ascertained and subjected to a plausibility check. A received plausibility-checked output signal is ascertained, having at least one item of information about the direction of change in the ethanol content of the fuel mixture.

5 Claims, 2 Drawing Sheets

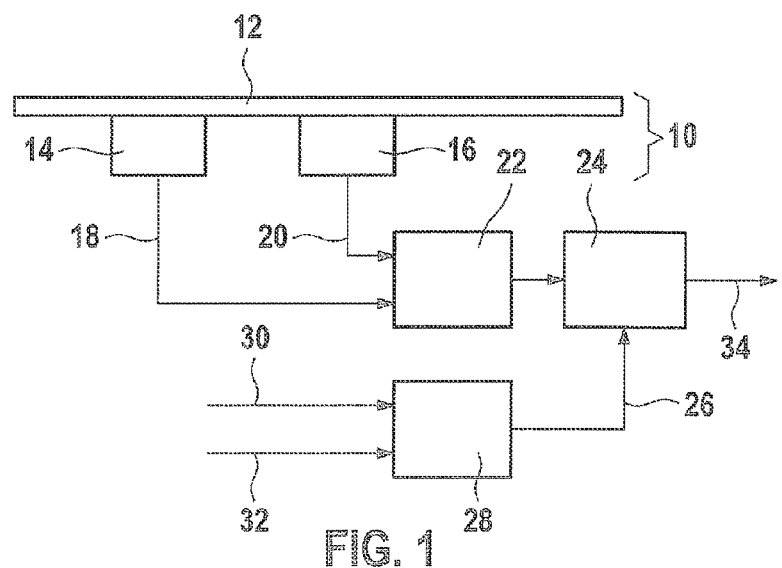
FIG. 1
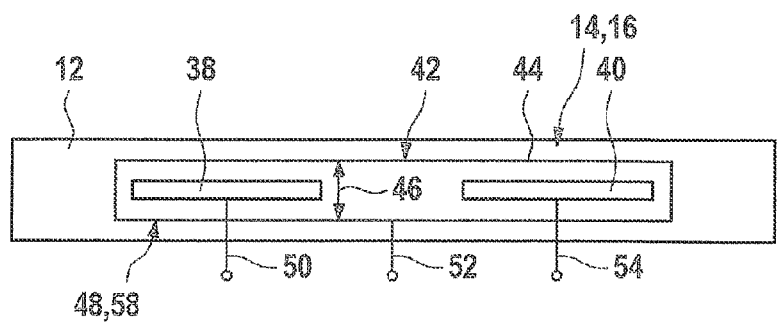
FIG. 2
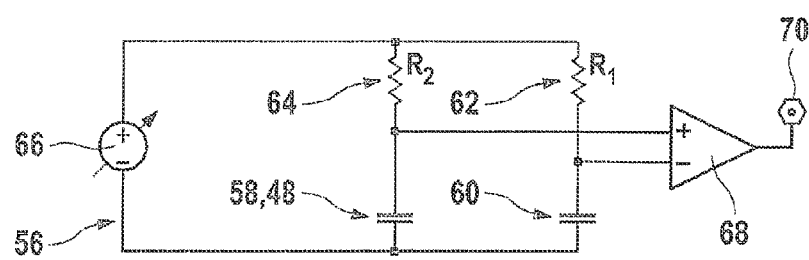
FIG. 3.1

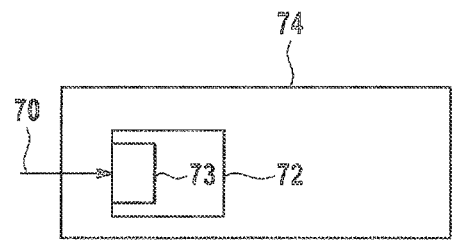
FIG. 3.2
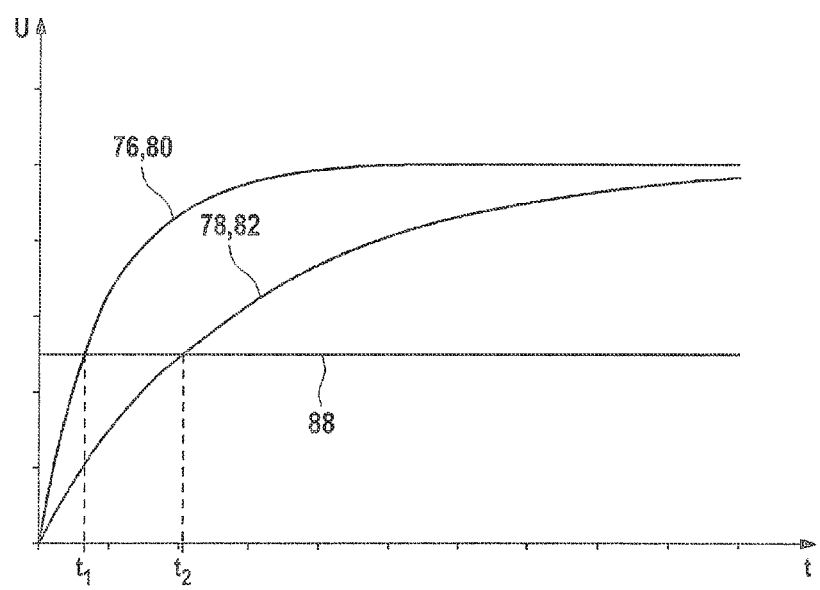
FIG. 4

DEVICE FOR MEASURING A COMPOSITION OF A FUEL MIXTURE

FIELD OF THE INVENTION

The present invention is directed to a method and a device for determining a composition of a fuel mixture, in particular for determining the ethanol content and/or a water component in the fuel mixture.

BACKGROUND INFORMATION

It is understood that there are methods and devices for determining compositions of fuel mixtures. For example, fuel mixtures are increasingly used in motor vehicles which are able to handle an admixture of ethanol and/or other alcohols, in addition to the proper mineral oil fuels. Flex-fuel vehicles which may be operated with variable ethanol/gasoline mixtures are known. The parameters of the engine control unit of the motor vehicle are adapted to the composition of each fuel mixture. Different concepts are in effect in different areas of the world. While in the U.S., usually only the essential adjustments of the engine control unit to the fuel mixture are made so far in order to be able to offer flex-fuel vehicles at all, efficiency and performance improvements are typically sought in Europe. In particular, however, the latter usually presupposes a precise knowledge of the composition of the fuel mixture, in particular an ethanol-fuel mixing ratio, in order to determine the optimal engine control parameters.

The ethanol-fuel mixing ratio is usually determined on the basis of available measured variables using software in the control unit itself, or this mixing ratio may be detected using an ethanol sensor. Such ethanol sensors may be based on numerous different measuring principles. Capacity measuring methods based on permittivity and conductivity determination are used in particular. As a rule, the permittivity of the fuel mixture is determined at frequencies up to approximately 1 MHz. However, one disadvantage of a simple permittivity determination (with temperature correction) at frequencies up to approximately 1 MHz is that in principle only the precise determination of the composition of mixtures of at most two components is possible when using these methods. This method cannot be used for detecting additional components of a fuel mixture in general.

To identify additional components such as $H_2O$, for example, measurements in the GHz range are necessary because the permittivity of alcohol, water and other polar components, e.g., interfering components, drops sharply here with an increase in frequency due to the orientation polarization. One example of such methods which operate in the GHz range is described in DE 34 12 704 A1. A device for measuring the alcohol content in a fuel mixture which may be used in a fuel line is used. The fuel line is made of a material which is permeable for high-frequency signals. A microwave chamber is situated outside of the fuel line, enclosing a portion of this fuel line. The microwave chamber has a pair of waveguides situated opposite one another with the fuel line between them. One of the waveguides is provided with an antenna section for transmission of microwaves from a microwave generator. The other microwave guide is provided with a receiving antenna section to receive microwaves passing through the fuel line. Microwaves received by the antenna section are detected by a detector and converted into d.c. voltage signals, which correspond to the strength of the received microwaves.

There are two different approaches for control of engines having a fuel composition varying from pure gasoline to a gasoline-ethanol mixture containing approximately 85% ethanol for flex-fuel systems. Using software-based systems, the deviation and the actual value of the λ sensor signal from the setpoint value of the applied mixture pre-control is observed. If this deviation occurs after a detected tank filling operation, then a change in the ethanol content is inferred. On the other hand, in sensor-based systems, the ethanol content of the fuel is measured directly using an ethanol sensor, usually located in the fuel supply line.

In both systems, the ignition angle is adjusted based on the engine control unit manipulated variables, for example, the fuel metering, as a function of the detected ethanol content.

The less expensive software-based systems have become popular in Brazil, which is today the most important market for flex-fuel vehicles. The European Union and NAFTA, which will become more important markets in the future, are being influenced by discussions by the vehicle manufacturers referring to the need for an ethanol sensor, i.e., a sensor-based system for detecting the composition of the fuel mixture. The strict OBD-II requirements (on-board diagnostics of the second generation) usually argue for sensor-based systems. A rapid and unambiguous allocation of a mixture deviation to the error source "error in fuel system" or to an altered fuel composition is presumably impossible to perform without using an ethanol sensor. In the case of saddle tanks, such as those described in DE 10 2007 039861 A1, for example, two interconnected tank chambers are provided. The saddle tank design is based on the fact that space must be provided for the drive shaft and the differential gear at the bottom of the tank in vehicles with rear-wheel drive. When filling the tank with smaller quantities, it may happen with saddle tanks that the tank quantity is stored in only one of the two tank chambers. If, for example, one of the tank chambers is filled with fuel grade E 85 and the second tank chamber is filled with E 110, a relatively rapid change in fuel composition will occur while driving when the fuel supply is switched from one tank chamber to the other tank chamber.

SUMMARY OF THE INVENTION

According to the exemplary embodiments and/or exemplary methods of the present invention, a differential sensor arrangement is described, whose basic configuration is characterized essentially in that two sensor elements spatially separate from one another are situated within the fuel line from the tank to the fuel injectors, so that fuel flows through these sensor elements sequentially. The two sensor elements generate a time-dependent output signal having a definite dependence on the ethanol content. The difference between the two output signals is determined in signal processing, which takes place within the engine control unit of the internal combustion engine, for example, and the differential signal is analyzed in a plausibility check. The time characteristic of the differential signal is analyzed in the plausibility check by determining the fuel flow rate and therefore checking on whether characteristic features of the differential signal are plausible for this flow rate. The flow rate is determined in the engine control unit by modeling the fuel system as a simple storage model with a known outflow rate corresponding essentially to the product of the engine rotational speed and the injection quantity per injection. The output signal contains at least the information about the direction of change in the ethanol content of the fuel mixture and optionally the absolute value of the change.

According to the exemplary embodiments and/or exemplary methods of the present invention, it is not the information about the absolute ethanol content but rather information about the change in the ethanol content of the fuel mixture which is utilized by the engine control within a flex-fuel system prior to the combustion of the fuel. If this change and the direction of change are detected by a sensor, the subsequent deviation in the mixture is to be assigned immediately and unambiguously to the altered ethanol content of the fuel mixture. Furthermore, an optimal ignition angle may be determined with the aid of the knock control, which may then intervene in the ignition angle in both control intervention directions, i.e., advance and retard adjustment.

A suitable design of the sensor elements for measuring the permittivity of the fuel includes, for example, two mutually insulated metallic electrodes integrated into the fuel line, for example, in the form of cylindrical tube sections. Additional mutually insulated metallic electrodes in the form of a tube having a larger diameter may also be provided. The electrodes form a capacitor including two concentric cylinders in each of which the dielectric medium is formed by the fuel. The electrical connection of the electronic analysis system, which is situated in the engine control unit, for example, is accomplished via various terminals.

A signal analysis of the differential signal within the scope of the plausibility check may take place, for example, using a circuit configuration having two capacitors and two resistors receiving power via an AC voltage. The difference in the voltages across the capacitors is determined with the aid of an operational amplifier and is available as voltage U_diff. This circuit configuration, which is configured as a bridge circuit, for example, is state of the art, U_diff and an A/D converter being available as a digital variable for further processing in the microcontroller.

In one embodiment, the AC voltage may be a sinusoidal voltage generated by the circuit described briefly above using an operational amplifier. If the analog-digital conversion of U_diff is made at selected points in time, for example, at the zero crossings of the sinusoidal voltage, then the amplitude and the phase shift of U_diff with respect to AC voltage Vs1 may be determined easily using an algorithm. These values change in a characteristic manner when the capacitances change temporarily in value due to the varying fuel composition flowing through them.

Another possible embodiment makes use of the properties of the microcontroller, which is already present in the engine control unit. The AC voltage Vs1 is supplied as a square-wave voltage, for example, through known programming of a counter and output of the signal via a digital output board of the microcontroller. This yields a time-dependent differential voltage per pulse of square-wave voltage Vs1, which may be processed further again after analog-digital conversion in an algorithm.

The exemplary embodiments and/or exemplary methods of the present invention are described in greater detail below with reference to the drawings.

BRIEF DESCRIPTION OF THE DRAWINGS

FIG. 1 shows the differential sensor arrangement according to the present invention in a schematic diagram.

FIG. 2 shows the design of sensor elements for measuring the permittivity of the fuel mixture.

FIG. 3.1 shows a circuit configuration for signal analysis.

FIG. 3.2 shows a schematic diagram of an engine control unit having a microcontroller.

FIG. 4 shows the voltage curve for two time constants across the capacitors plotted as a function of time.

DETAILED DESCRIPTION

The diagram in FIG. 1 is a schematic diagram of a sensor arrangement according to the exemplary embodiments and/or exemplary methods of the present invention.

FIG. 1 shows a sensor 10, including a first sensor element 14 and a second sensor element 16, which are spatially separated from one another and are connected to fuel line 12 through which fuel flows. As already mentioned at the outset, the fuel flowing in fuel line 12 is a fuel mixture possibly containing ethanol, water and even other admixture components, the level of which is ascertained by the sensor arrangement according to the present invention.

Fuel line 12 extends from the tank (not shown in FIG. 1) to the fuel injectors of the internal combustion engine. The two sensor elements assigned to fuel line 12, i.e., first sensor element 14 and second sensor element 16, are spatially separated from one another and have fuel flowing through them sequentially. Both sensor elements 14, 16 each generate a time-dependent output signal, first sensor 14 generating a first output signal 18, second sensor element 16 generating a second time-dependent output signal 20. Both time-dependent output signals 18, 20 have a definite dependence on the ethanol content of the fuel mixture.

First time-dependent output signal 18 and second time-dependent output signal 20 are processed further within a signal processing unit, which may take place in an engine control unit. In a difference-forming stage 22, the difference between first time-dependent output signal 18 and second time-dependent output signal 20 of sensor elements 14, 16, which are spatially separated from one another, is determined. The obtained signal is analyzed in a plausibility check stage 24 downstream from difference-forming stage 22.

The obtained output signal of difference-forming stage 22 is checked for plausibility in plausibility check stage 24 by determining a flow rate 26 at which fuel flows in fuel line 12. Based on the value for obtained flow rate 26 of the fuel, it is checked whether or not the characteristic features of the differential signal, which is ascertained in difference-forming stage 22, are plausible for the ascertained corresponding flow rate 26 for the fuel in fuel line 12. The schematic diagram in FIG. 1 shows that plausibility check stage 24 receives, on the one hand, the output signal, i.e., the differential signal of difference-forming stage 22, and on the other hand, ascertained flow rate 26. Flow rate 26 is in turn determined in the engine control unit, for example, by modeling the fuel system as a storage model, as indicated by reference numeral 28. Input variables of the storage model, which assumes a known outward flow, include engine rotational speed 30 of the internal combustion engine and an injection quantity per injection 32 of the internal combustion engine. Within the scope of storage model 28, flow rate 26 of the fuel in fuel line 12 is determined from the product of engine rotational speed 30 and the injection quantity per injection 32 as input variables. Output signal 34, which is output to plausibility check stage 24 at the output end, contains at least information about the direction of change in the ethanol content within the fuel mixture and optionally also the absolute value of the change.

The control unit of an engine or an internal combustion engine of a motor vehicle in flex-fuel operation requires only the information about the change in the ethanol content prior to the combustion of the fuel and only optionally the knowledge about the absolute prevailing ethanol content of the fuel mixture. If the change in ethanol content and the direction of change are ascertained by the sensor arrangement according to the present invention, a subsequent mixture deviation may then be assigned immediately and unambiguously to the altered ethanol content. Depending on the change in the mixture deviation, an optimal ignition angle may be determined within the engine control unit by knock control, which may then intervene in both control intervention directions, i.e., advance and retard adjustment with respect to the ignition angle.

The diagram according to FIG. 2 illustrates one possible embodiment of the sensor elements of the sensor according to the present invention.

Using the embodiment of sensor 10 shown in FIG. 2, a permittivity of the fuel is then measured. In addition to measuring the permittivity, which is in particular a complex permittivity, a permittivity number, in particular a complex permittivity number, an absorption, in particular a complex absorption, a transmission, in particular a complex transmission, may be included. The complex variables mentioned above are to be understood as variables which include an amplitude and a phase. The permittivity, which is often represented by $\in$, describes the permeability of materials for electrical fields. This is a material property of dielectric media and at least only weakly electrically conductive materials, this property being manifested when the materials are exposed to electric fields. This represents the proportionality constant between electric flux density D and electrical field E: $D=\in \times E$. The permittivity number, which is frequently also referred to as $\in_r$ or as the relative permittivity, is the ratio of permittivity $\in$ to electrical field constant $\in_0$ (permittivity of the vacuum): $\in_r = \in/\in_0$. Permittivity number $\in_r$ thus characterizes the field-weakening effects of electrical polarization within electrically insulating materials. Within the scope of the present invention, electrical susceptibility $\kappa = \in -1$ is equivalent to permittivity number $\in_r$. No distinction is made conceptually between the susceptibility and the permittivity number in the sense of the present invention.

Both the permittivity and the susceptibility of the fuel are measurable using the design of sensor elements 14, 16 according to FIG. 2. There are two mutually insulated metallic electrodes 38 and 40 inside fuel line 12 through which fuel is flowing. A first metallic electrode is identified by reference numeral 38 and another second metallic electrode has been identified by reference numeral 40. Both metallic electrodes 38 and 40 are configured in the form of cylindrical tube sections.

The diagram in FIG. 2 shows that both metallic electrodes 38 and 40 are surrounded by a third metallic electrode 42, which is in the form of a tube 44 and is insulated with respect to first metallic electrode 38 and second metallic electrode 40. The diagram in FIG. 2 shows that a diameter 46 of third metallic electrode 42, which is configured as a tube 44, is larger than the corresponding diameter of the cylindrical tube sections of first metallic electrode 38 and second metallic electrode 40.

Due to this configuration, first metallic electrode 38 and third metallic electrode 42 in the form of a tube 44 form a first capacitor 48, 58, whereas second metallic electrode 40 in the form of a cylindrical tube section forms another second capacitor 60 in third metallic electrode 42 in the form of tube 44 with an enlarged diameter 46 surrounding this electrode. Fuel flowing in fuel line 12 forms the dielectric medium of first capacitor 48 and 58 and of second capacitor 60. An electrical connection of capacitors 48, 58 and 60 to the electronic analyzer is accomplished via terminals 50, 52, 54, as shown schematically in FIG. 2.

The diagram according to FIG. 3.1 shows a circuit configuration with which the time-dependent output signals obtained from the capacitors according to FIG. 2 as a function of the ethanol content in the fuel mixture may be analyzed. FIG. 3.1 shows a circuit configuration 56 including first capacitor 48 and 58 as well as second capacitor 60. First capacitor 48, 58 and second capacitor 60 are configured as described above in conjunction with FIG. 2. Circuit configuration 56 according to the diagram in FIG. 3.1 includes a first resistor 62 ($R_1$) and another second resistor 64 ($R_2$). First capacitor 48, 58 and second capacitor 60 are supplied with an AC voltage Vs1 from an AC voltage source 66 via both resistors 62 and 64. The differences in the voltages across first capacitor 48, 58 and second capacitor 60 are determined with the aid of an operational amplifier 68 and is available as voltage difference U_diff (cf. reference numeral 70). Circuit configuration 56 shown in FIG. 3.1 corresponds to a bridge circuit. Voltage difference 70 is supplied as a digital variable using an A/D converter 73 for further processing in a microcontroller 72 and picked up in an engine control unit 74, as shown in FIG. 3.2. Microcontroller 72, which processes the input signals of the engine control unit, for example, the engine rotational speed, and ascertains the calculated output signals, for example, the duration of the fuel injection, outputs the output signals to actuators (not shown here) of the engine control unit. Microcontroller 72 may includes A/D converter 73 shown in FIG. 3.2.

With respect to circuit configuration 56 according to the diagram in FIG. 3.1, it should be pointed out that AC voltage source 66 is capable of supplying an AC voltage in the form of a sinusoidal voltage as well as using a square-wave excitation. As shown in FIG. 3.1, a sinusoidal AC voltage Vs1 may be generated with the aid of an operational amplifier (not shown here). Operational amplifier 68 carries out the difference formation. If an analog-digital conversion of voltage difference U_diff (cf. reference numeral 70) is carried out at selected points in time, for example, at the zero crossings of AC voltage Vs1 (66), then the amplitude and phase shift of differential voltage U_diff, 70 with respect to AC voltage Vs1 66 may be determined with little effort using an algorithm. These values undergo characteristic changes when the capacitance of second capacitor 60 changes temporarily in its value in relation to the capacitance of first capacitor 48, 58 due to the changing fuel composition flowing through it. This change in fuel composition is detected directly for the capacitors, which are configured according to the diagram in FIG. 2, in which the fuel flowing through represents the dielectric medium of first capacitor 48, 58 and of second capacitor 60.

In another embodiment variant of a signal analysis, the properties of a microcontroller 72, which is already present in engine control unit 74, may be utilized (cf. FIG. 3.2). AC voltage 66 is in the form of a square-wave voltage, which is obtained, for example, by programming a counter and by output of a signal via a digital output port of microcontroller 72. This yields a time-dependent differential voltage per pulse of a square-wave voltage Vs1, i.e., square-wave AC voltage Vs1 66. This is in turn to be processed further after an analog-digital conversion using an algorithm. In another embodiment, the control of the counter for synchronization of two time measurements by microcontroller 72 is used below as the example of a square-wave excitation. FIG. 4 shows the result of these time measurements. FIG. 4 shows the curve of two voltages for two time constants, wherein the two voltage curves differ by a factor of 3.

FIG. 4 shows the curve of a first voltage 76 (U1) for a first time constant R1×C1 and the curve of a second voltage 78 (U2) for a second time constant R2×C2 (cf. reference numeral 82). First voltage 76 differs from second voltage 78 by a factor of 3 in the rate of rise of the voltage. After applying a positive sudden voltage change at t=0, the curves of first voltage 76 for first time constant 80 and the curve of second voltage 78 for second time constant 82 are established according to the voltage curves in FIG. 4. First voltage 76 and second voltage 78 are fed to a digital input of microcontroller 72 here, each being connected to a timer structure. Reference numeral 88 denotes a switching threshold, the individual values for first voltage 76 and second voltage 78 generating, at measured times $t_1$, a first measured time 84, and $t_2$, i.e., a second measured time 86 when this switching threshold is reached. Since the difference between measured times $t_1$ and $t_2$ is a measure of the ratio of the two values of the capacitances of first capacitor 48, 58 and of second capacitor 60.

A plurality of measurements according to the method described above is possible due to a frequency of the feed voltage, i.e., AC voltage 66, which is comparatively high in comparison with the change in the capacitances of first capacitor 48, 58 and of second capacitor 60 over time with a change in the fuel composition. Individual electrical interferences in the sensor signals may thus be suppressed effectively by averaging. Basically, first voltages 76 and second voltages 78 or first measured times $t_1$ and second measured times $t_2$, which differ slightly from one another, are generated in first capacitance of first capacitors 48, 58 as well as in second capacitance of second capacitor 60 due to fuel flows of a constant permittivity $\in$. The causes for this are minor asymmetries due to the design and cabling as well as the fact that switching threshold 88 of the level detection of the digital inputs is not exactly the same for the method described here for time measurement. However, since there is not a changing fuel composition in the area of sensor 10 in the short run, the signal analysis according to the diagram in FIG. 3.1 is expanded by offset compensation. For this purpose, voltage difference 70 U_diff and the difference between first measured time $t_1$ (84) and second measured time $t_2$ (86) are filtered through a low-pass filter using a time constant of several minutes, for example, then this output signal is subtracted from the signal for voltage difference U_diff or the time difference between first measured time $t_1$ (84) and second measured time $t_2$ (86). Such an offset compensation may be accomplished by an analog circuit, but an algorithmic implementation in microcontroller 72 which is integrated into engine control unit 74 (cf. FIG. 3.2) seems to be more advantageous.

What is claimed is:

1. A device for determining a composition of a fuel mixture, comprising:
    a first sensor element in a fuel line; and
    a second sensor element in the fuel line, wherein the first sensor element and the second sensor element are spatially separated from one another in the fuel line;
    wherein each of the sensor elements include a first metallic electrode and a second metallic electrode, wherein the first metallic electrode and the second metallic electrode are surrounded by a third metallic electrode,
    wherein the first metallic electrode and the third metallic electrode, configured as a tube, form a first capacitor,
    wherein the second metallic electrode and the third metallic electrode, configured as a tube, form a second capacitor, and
    wherein a dielectric medium of the first capacitor and the second capacitor is formed by fuel flowing in the fuel line.

2. The device of claim 1, wherein the first metallic electrode and the second metallic electrode are formed by cylindrical tube sections, each being surrounded by the third metallic electrode configured as a tube, its diameter exceeding that of the cylindrical tube sections.

3. The device of claim 1, wherein the capacitors are connected to an AC voltage source, which generates an AC voltage in one of a sinusoidal-wave and a square-wave form Vs1.

4. The device of claim 3, further comprising:
    a circuit configuration having an operational amplifier which measures a differential voltage of voltages, which drop across the capacitors, and ascertains another differential voltage.

5. The device of claim 1, wherein the fuel flows laterally and sequentially through the sensor elements situated spatially separated from one another, wherein the sensor elements generate time-dependent output signals, which depend on the ethanol content of the fuel mixture, wherein a difference is ascertained between the time-dependent output signals and subjected to a plausibility check, and wherein a plausibility-checked output signal is ascertained which contains at least one item of information about a direction of change in an ethanol content of the fuel mixture.

* * * * *